US011266779B2

(12) United States Patent
Mason et al.

(10) Patent No.: US 11,266,779 B2
(45) Date of Patent: Mar. 8, 2022

(54) IV SET SPIKE WITH ENHANCED REMOVAL FORCE

(71) Applicant: CareFusion 303, Inc., San Diego, CA (US)

(72) Inventors: Gene Mason, La Habra, CA (US); George Mansour, Diamond Bar, CA (US); Ryan Callahan, Long Beach, CA (US); Edmond Yu, Chino Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 302 days.

(21) Appl. No.: 16/292,122

(22) Filed: Mar. 4, 2019

(65) Prior Publication Data
US 2020/0282133 A1    Sep. 10, 2020

(51) Int. Cl.
*A61M 5/162*    (2006.01)
*A61J 1/20*    (2006.01)
(Continued)

(52) U.S. Cl.
CPC ............ *A61M 5/162* (2013.01); *A61J 1/1406* (2013.01); *A61J 1/2006* (2015.05); *A61J 1/10* (2013.01); *A61M 2039/1072* (2013.01)

(58) Field of Classification Search
CPC .. A61M 5/162; A61M 25/0097; A61M 25/01; A61M 25/0136; A61M 39/1011; A61M 2025/0681; A61M 2005/3247; A61M 5/3134; A61M 5/3204; A61M 5/20; A61M 5/3137; A61M 5/3157;
(Continued)

(56) References Cited

U.S. PATENT DOCUMENTS 3,667,464 A * 6/1972 Alligood, Jr. ........ A61M 5/1411
604/254
3,896,805 A * 7/1975 Weingarten ........... A61M 5/284
604/191
(Continued)

FOREIGN PATENT DOCUMENTS

| EP | 0050459 A1 * | 4/1982 | ............ A61M 5/162 |
| WO | WO-2007047200 A1 | 4/2007 | |
| WO | WO-2012103141 A1 * | 8/2012 | .......... A61M 5/3137 |

OTHER PUBLICATIONS

"Integral." Merriam-Webster.com Dictionary, Merriam-Webster, https://www.merriam-webster.com/dictionary/integral. Accessed Jan. 26, 2021. (Year: 2021).*

(Continued)

*Primary Examiner* — Benjamin J Klein
(74) *Attorney, Agent, or Firm* — Morgan, Lewis & Bockius LLP (57) ABSTRACT

IV spikes are described herein. An IV spike includes a spike body. The spike body can be formed of a first material and can include a spike portion converging to a point. The IV spike further includes at least one spike flow port formed through the spike body. The IV spike further includes a lower flow port in fluid communication with the at least one spike flow port. The IV spike can also include an overmolded engagement feature disposed around the spike body, wherein the overmolded engagement feature comprises a second material and is configured to retain the IV spike within an IV container.

12 Claims, 7 Drawing Sheets

(51) Int. Cl.
  *A61J 1/14* (2006.01)
  *A61M 39/10* (2006.01)
  *A61J 1/10* (2006.01)

(58) Field of Classification Search
  CPC ........ A61M 5/3202; A61M 2005/2006; A61M 2005/2026; A61M 2005/206; A61M 2005/3125; A61M 2205/584; A61M 2205/586; A61M 2207/00; A61M 2025/09125; A61M 25/0105; A61M 25/0147; A61M 5/1411; A61M 2039/1072; A61M 2205/0216; A61M 2205/0238; A61J 1/2006; A61J 1/1406; A61J 1/10; A61B 5/150274; A61B 5/150259; Y10T 29/49826
  See application file for complete search history.

(56) References Cited

U.S. PATENT DOCUMENTS

| | | | | |
|---|---|---|---|---|
| 5,211,638 A * | 5/1993 | Dudar | ........... | A61J 1/2089 604/411 |
| 5,797,897 A * | 8/1998 | Jepson | ........... | A61J 1/2089 604/239 |
| 6,113,068 A * | 9/2000 | Ryan | ........... | A61M 39/045 251/149.4 |
| 6,635,044 B2 * | 10/2003 | Lopez | ........... | A61M 39/10 604/500 |
| 6,719,719 B2 * | 4/2004 | Carmel | ........... | A61J 1/2089 604/191 |
| 7,198,746 B1 * | 4/2007 | Kobayashi | ........... | A61M 5/1411 264/249 |
| 7,635,344 B2 * | 12/2009 | Tennican | ........... | A61J 1/2096 604/88 |
| 9,216,138 B2 * | 12/2015 | Finke | ........... | A61J 1/2089 |
| 9,550,024 B2 * | 1/2017 | Hanner | ........... | A61M 5/1407 |
| 10,537,495 B2 * | 1/2020 | Ivosevic | ........... | A61J 1/201 |
| 10,617,817 B2 * | 4/2020 | Hwang | ........... | A61L 29/16 |
| 2003/0191445 A1 * | 10/2003 | Wallen | ........... | A61M 5/1408 604/411 |
| 2005/0277906 A1 * | 12/2005 | Brugger | ........... | A61M 5/162 604/411 |
| 2011/0049866 A1 * | 3/2011 | Trombley, III | ........ | A61M 5/007 285/20 |
| 2011/0077621 A1 * | 3/2011 | Graham | ........... | A61M 25/01 604/528 |
| 2012/0078215 A1 * | 3/2012 | Finke | ........... | A61M 3/00 604/414 |
| 2012/0184938 A1 * | 7/2012 | Lev | ........... | B65D 51/002 604/414 |
| 2020/0214936 A1 * | 7/2020 | Battaglia, Jr. | ........... | A61J 1/16 |

OTHER PUBLICATIONS

International Search Report and Written Opinion for Application No. PCT/US2020/021007, dated Jun. 9, 2020, 14 pages.

\* cited by examiner

IV SET SPIKE WITH ENHANCED REMOVAL FORCE

FIELD OF THE INVENTION

The present disclosure generally relates to IV spikes, and, in particular, to IV spikes with engagement features.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV container, bag, or bottle. An IV set can include an IV spike to pierce a membrane of an IV container to allow the medical fluid to exit the IV container. Once an IV spike is advanced through the membrane of the IV container, medical fluid can flow through the IV spike to the IV set.

In some applications, the IV container can be a blow molded polyethylene bottle. The blow molded bottles may have a thin wall thickness and low compliance. In certain applications, during the use of IV sets, the IV spike may be inadvertently removed from the IV container.

SUMMARY

The disclosed subject matter relates to IV spikes with engagement features. In certain embodiments an IV spike comprises a spike body comprising a first material and a spike portion converging to a point; at least one spike flow port formed through the spike body; a lower flow port in fluid communication with the at least one spike flow port; and an overmolded engagement feature disposed around the spike body, wherein the overmolded engagement feature comprises a second material and is configured to retain the IV spike within an IV container.

In certain embodiments, an IV spike comprises a spike body comprising a first material and a spike portion converging to a point; at least one spike flow port formed through the spike body; a lower flow port in fluid communication with the at least one spike flow port; and an engagement feature extending radially away from the spike body wherein the engagement feature is configured to retain the IV spike within an IV container.

In certain embodiments, a method to transfer fluid from an IV container to a drip chamber comprises engaging an engagement feature of an IV spike against a membrane of the IV container; and directing flow from the IV container to the drip chamber through the IV spike.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed IV spike incorporates features to engage and seal against various types of IV containers. The IV spike can engage with portions of IV containers to retain the IV spike within the IV container. The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid to a patient by a medical practitioner using the disclosed IV spike, it is to be understood that this description is only an example of usage and does not limit the scope of the claims. Various aspects of the disclosed IV spike may be used in any application where it is desirable to prevent inadvertent removal of an IV spike.

The disclosed IV spike overcomes several challenges discovered with respect to the operation and setup of certain IV sets. One challenge with certain conventional IV spikes is that they may have a low removal force (less than one pound of force) from IV containers of varying or different construction. Because certain conventional IV spikes may be removed with low amounts of force, certain conventional IV spikes may be inadvertently or unintentionally removed from the IV container, interrupting the medical treatment.

Therefore, in accordance with the present disclosure, it is advantageous to provide an IV spike as described herein that can be securely engaged within different IV containers. The disclosed IV spike provides engagement features to engage with various IV containers. Advantageously, the disclosed IV spike allows for clinicians to consistently and reliably utilize the IV spike without inadvertently removing the IV spike from the IV containers. Further, the disclosed IV spike can be reliably used with a variety of IV containers, including polyvinyl chloride (PVC) IV bags and/or blow molded polyethylene infusion bottles. Additionally, the IV spike can seal against IV containers to prevent leaks.

An example of an IV spike that can engage with various IV containers is now described.

Figure 1:
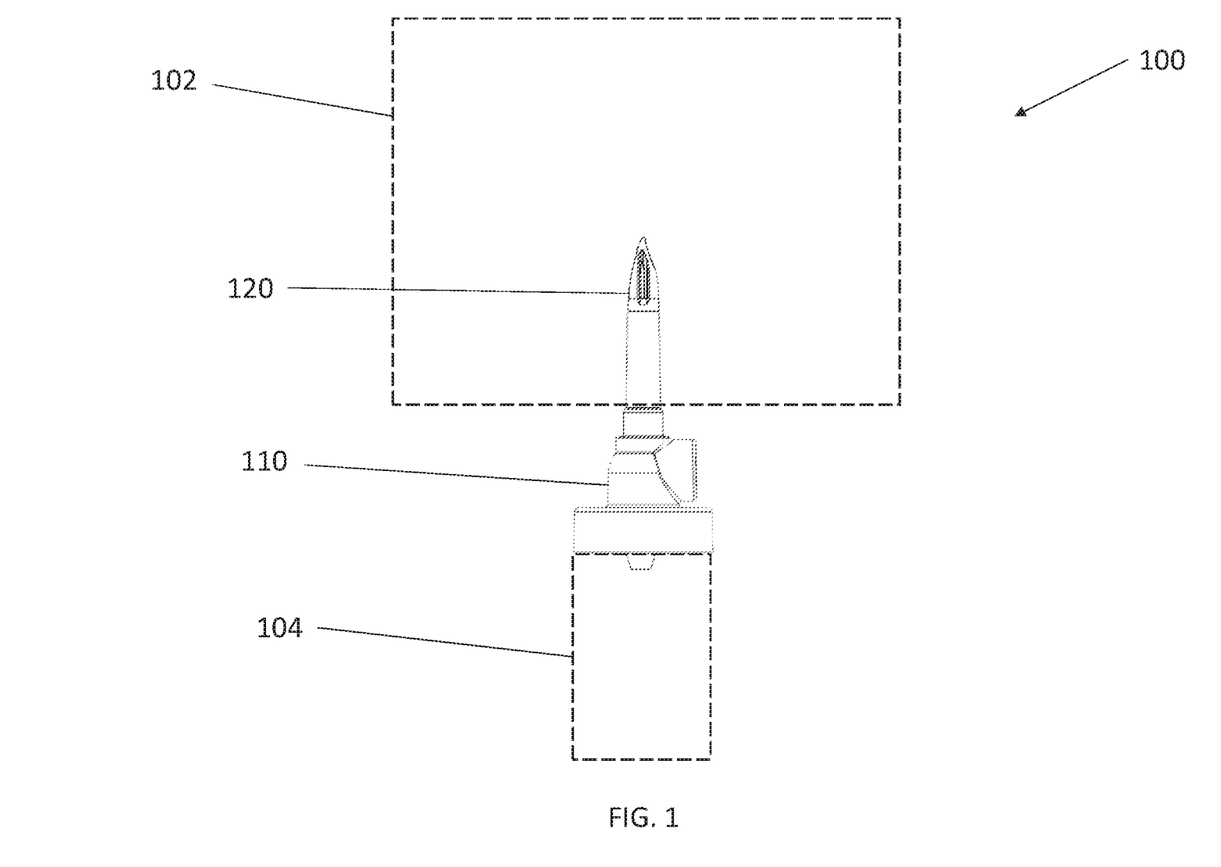
FIG. 1 is an elevation view of an IV set, in accordance with various aspects of the present disclosure.

FIG. 1 is an elevation view of an IV set 100, in accordance with various aspects of the present disclosure. In the depicted example, the IV set 100 can provide medical fluid from an IV container, bag, or bottle 102 to a patient.

As illustrated, an IV spike 110 facilitates the transfer of fluid from the IV container 102 to the patient via the drip chamber 104. During operation, the IV spike 110 is advanced through the IV container 102 to pierce the membrane of the sealed IV container 102. As the IV spike 110 is advanced, the membrane of the IV container 102 is displaced. After the IV spike 110 is introduced, engagement features of the IV spike 110 retain the IV spike 110 within the IV container 102. Further, the engagement features of the IV spike 110 can seal the IV spike 110 against the IV container 102.

As illustrated, the IV container 102 can be any suitable container to store medical fluid. In some embodiments, the IV container 102 is a PVC IV bag. In some applications, such as some developing countries, the IV container 102 can vary in construction from a PVC IV bag. For example, the IV container 102 can be a blow molded polyethylene infusion bottle. Additionally, the IV container 102 can have thinner wall construction or lower compliance compared to a PVC IV bag.

Advantageously, engagement features of the IV spike 110 can engage with IV containers 102 that have thinner wall construction or lower compliance compared a PVC IV bag to ensure that the IV spike 110 is securely engaged. Optionally, the IV spike 110 can be used with a PVC IV bag.

After the IV spike 110 is introduced into the IV container 102, medical fluid from the IV container 102 is permitted to flow through the IV spike 110 to the drip chamber 104 and to the patient.

Figure 2:
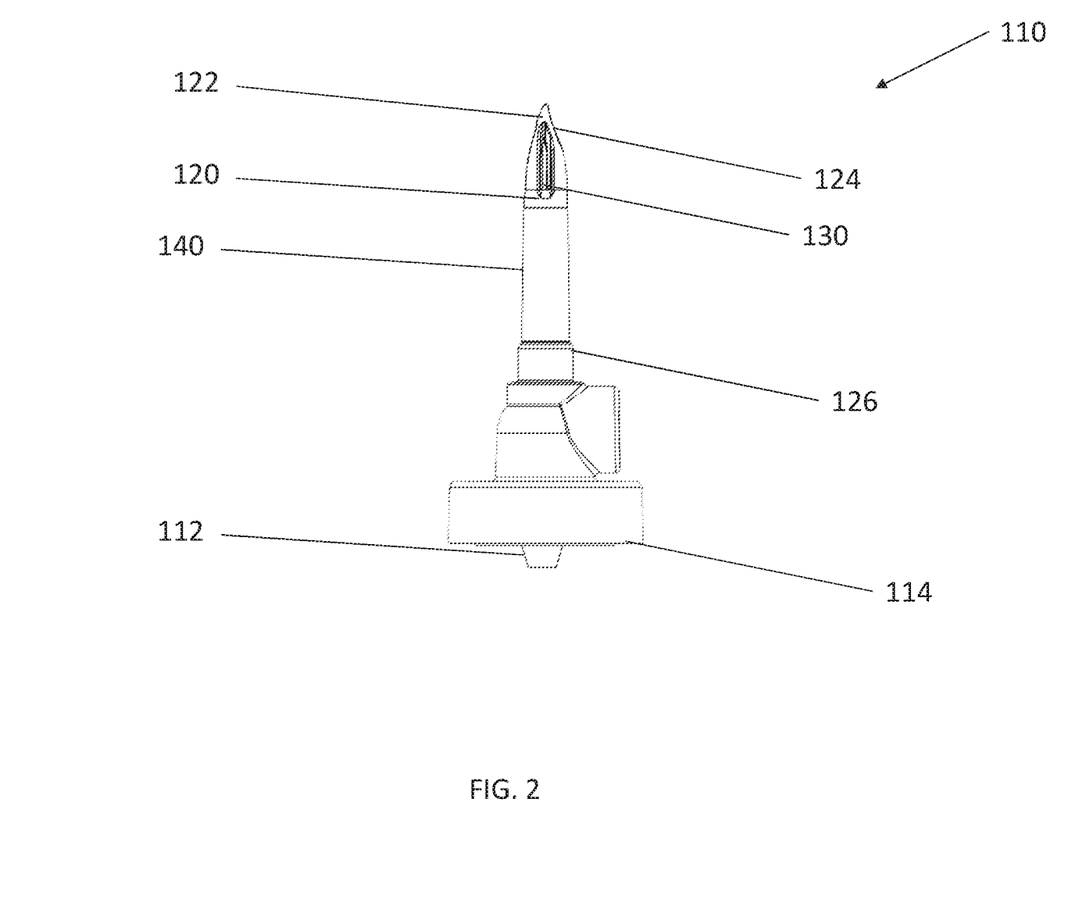
FIG. 2 is an elevation view of an IV spike for use with the IV set of FIG. 1, in accordance with various aspects of the present disclosure.

FIG. 2 is an elevation view of an IV spike 110 for use with the IV set 100 of FIG. 1, in accordance with various aspects of the present disclosure. In the illustrated embodiment, the IV spike 110 can be advanced through a membrane of an IV container to permit the outflow of the medical fluid within the IV container.

In the depicted example, the spike body 120 pierces and displaces the membrane of the IV container. The spike body 120 extends from a base portion 126 and converges to a spike portion 122. In some embodiments, the spike body 120 is generally an elongate member. Optionally, the spike body 120 can have a generally cylindrical shape. The spike body 120 can be formed from a generally rigid material, including, but not limited to acrylonitrile butadiene styrene (ABS) plastic.

As illustrated, the spike portion 122 converges to a point or more generally to a portion of reduced radius relative to the spike body 120. Optionally, the spike portion 122 can have a bevel 124. During operation, as the IV spike 110 is advanced, the spike portion 122 can pierce or rupture the membrane of the IV container, permitting the spike body 120 to displace the membrane and be advanced into the IV container.

Once the spike body 120 has ruptured the membrane and is advanced into the IV container, the overmold 140 can retain the IV spike 110 within the IV container. For example, the overmold 140 can engage with the edges of the membrane or the IV container surrounding the IV spike 110.

Upon insertion of the spike body 120 into the IV container, the overmold 140 can be sufficiently compliant to elastically deform to compress through the puncture site and/or expand past the puncture site. As a result, the overmold 140 can have a greater surface area in contact with the membrane of the IV container. In some embodiments, the overmold 140 can expand to seal and/or minimize small gaps between the IV spike 110 and the membrane of the IV container to prevent or abate leaks, effectively acting as a gasket. Optionally, edges of the membrane of the IV container can engage or "dig in" to the compliant material of the overmold 140.

In the depicted example, the overmold 140 can be formed of a compliant material, such as a soft polymer, a thermoplastic elastomer (TPE) and/or silicone. In some embodiments, the overmold 140 can be formed from a material with a greater compliance (lower durometer) than the material of the spike body 120.

Furthermore, the overmold 140 can have a sufficient coefficient of friction to frictionally engage the overmold 140 against the membrane of the IV container. In some embodiments, the coefficient of friction of the material of the overmold 140 is greater than the coefficient of friction of the material of the spike body 120.

As illustrated, the overmold 140 is cylindrically and/or circumferentially formed over the spike body 120. In some embodiments, the overmold 140 is formed as a cylindrical body or as a skin over the spike body 120. Optionally, the overmold 140 can extend along an axial length of the spike body 120. The overmold 140 can be formed by a "second shot" during the molding process of the IV spike 110.

Optionally, the overmold 140 can create a physical barrier that prevents the removal of the IV spike 110 from the IV container. For example, edges of the overmold 140 can engage the membrane of the IV container to prevent the removal of the IV spike 110 from the IV container.

Figure 3:
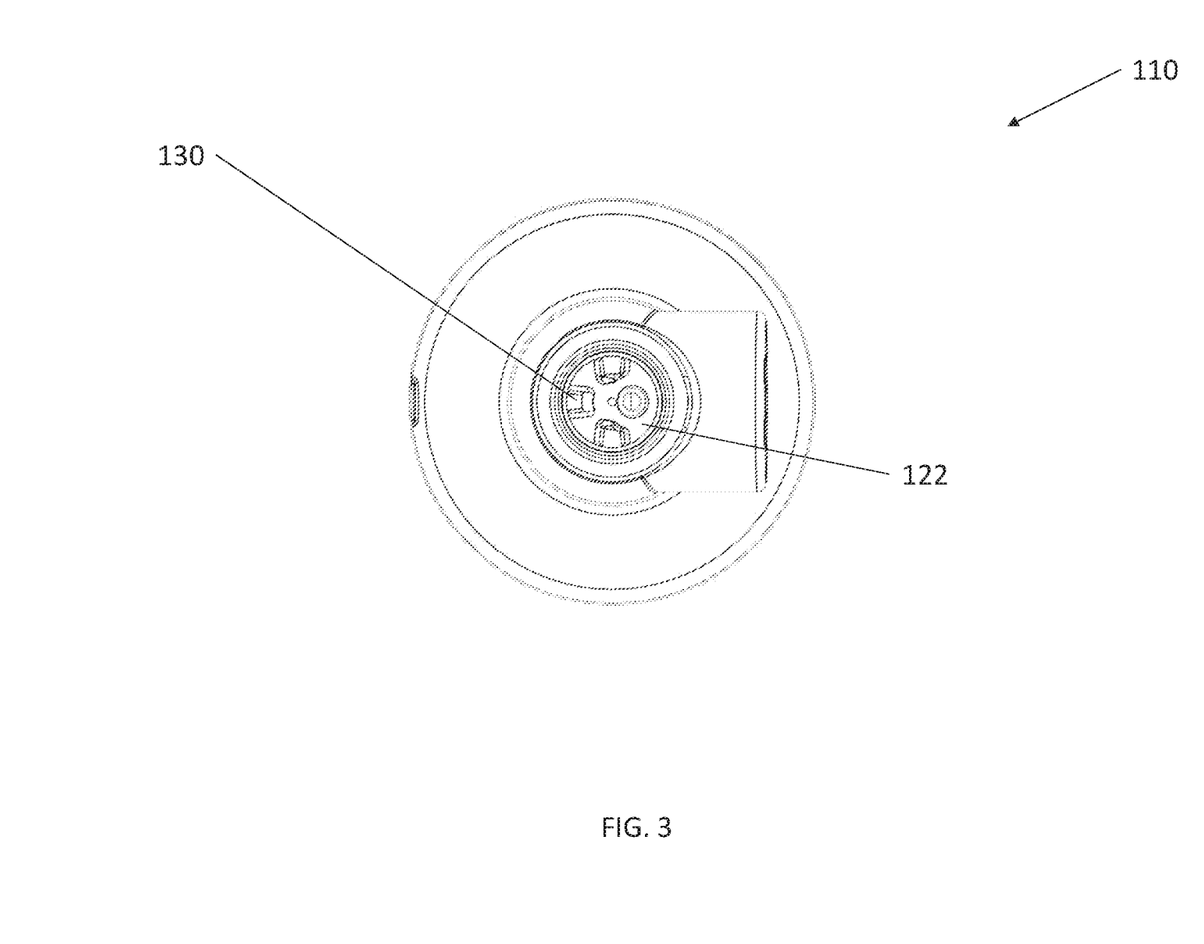
FIG. 3 is a top view of the IV spike of FIG. 2, in accordance with various aspects of the present disclosure.
Figure 4:
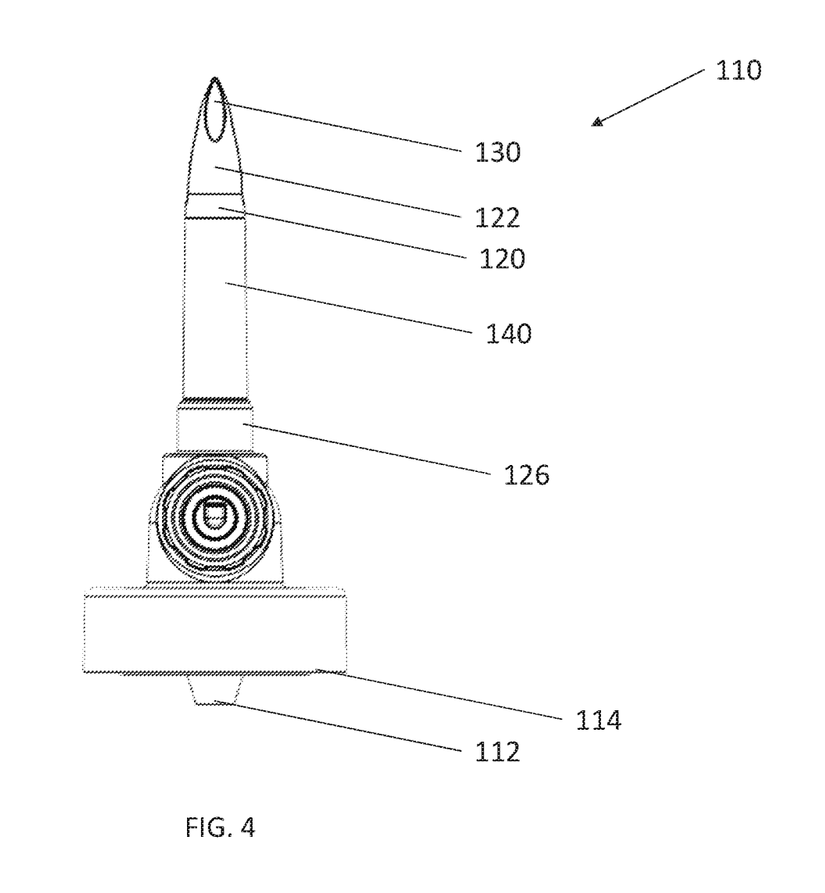
FIG. 4 is an elevation view of the IV spike of FIG. 2, in accordance with various aspects of the present disclosure.

FIG. 3 is a top view of the IV spike 110 of FIG. 2, in accordance with various aspects of the present disclosure. FIG. 4 is an elevation view of the IV spike 110 of FIG. 2, in accordance with various aspects of the present disclosure. With reference to FIGS. 2-4, after the IV spike 110 is introduced into the IV container, the IV spike 110 can facilitate the flow of medical fluid from the IV spike to the patient via the drip chamber.

In the depicted example, medical fluid flows from the spike flow ports 130, through the spike body 120 and exits the IV spike 110 via the lower flow port 112. As illustrated, the spike flow ports 130 can be formed adjacent to or through the spike portion 122 of the spike body 120. Optionally, the spike flow ports 130 can have an oblong cross-sectional profile. In some embodiments, the spike flow ports 130 are disposed above the overmold 140 to permit the flow of medical fluid and air through the spike flow ports 130. In the depicted example, the spike flow ports 130 are formed to continue through the spike body 120. The IV spike 110 can include one or more spike flow ports 130. For example, the IV spike 110 can include three spike flow ports 130.

As illustrated, the spike flow ports 130 are in fluid communication with the lower flow port 112. The lower flow port 112 allows fluid flow from the IV spike 110 to a drip chamber. The drip chamber can be coupled to the IV spike via the drip chamber connector 114.

Figure 5:
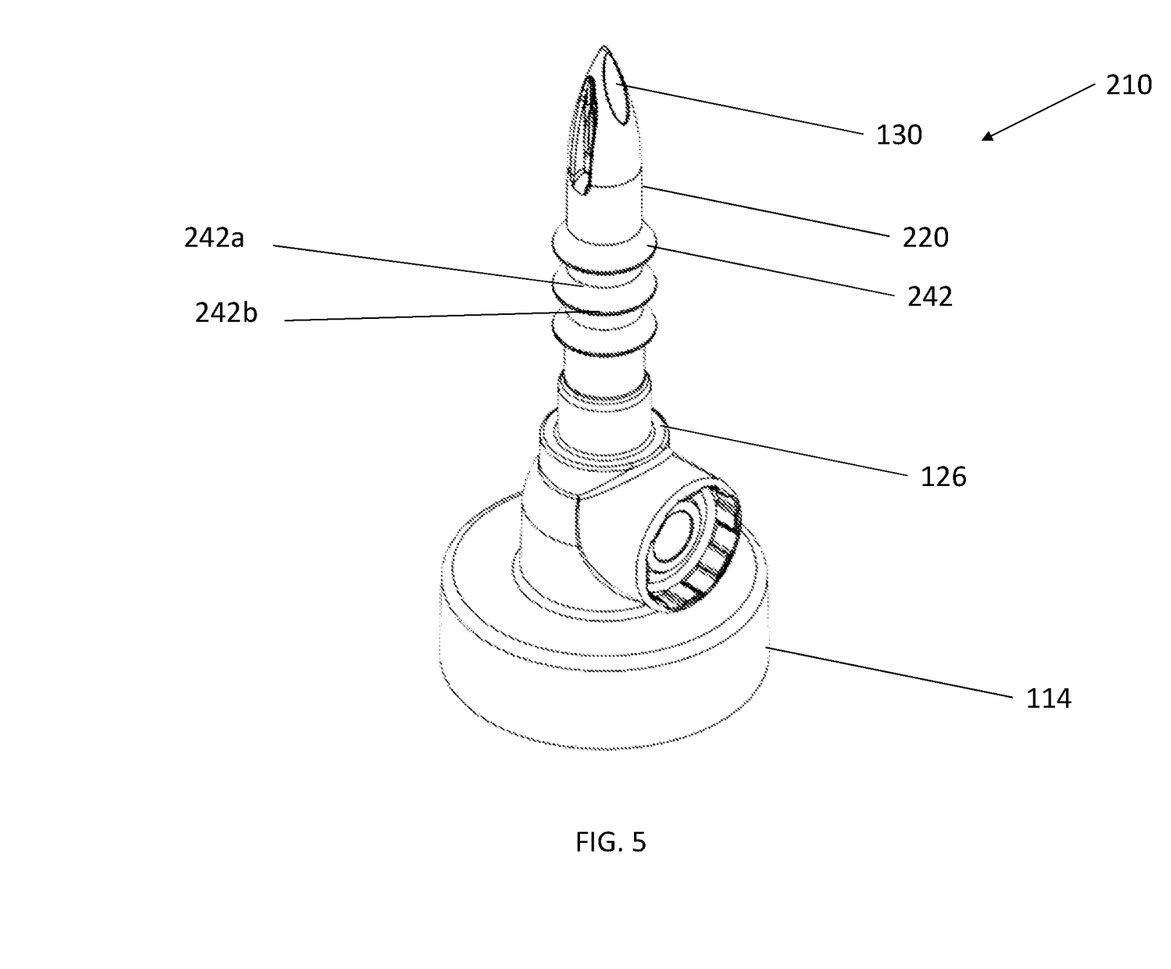
FIG. 5 is a perspective view of an IV spike for use with the IV set of FIG. 1, in accordance with various aspects of the present disclosure.

FIG. 5 is a perspective view of an IV spike 210 for use with the IV set 100 of FIG. 1, in accordance with various aspects of the present disclosure. In the depicted example, the IV spike 210 includes retention features 242 that create a physical barrier that prevent the removal of the IV spike 210 from the IV container.

In some embodiments, the retention features 242 extend radially away from the spike body 220. In the depicted example, the retention features 242 have a tapered or barbed shape that allows the retention features 242 to pass through the puncture site. As illustrated, the retention features 242 can be axially spaced apart. In the depicted example, each retention feature 242 includes a distal radius 242*a* and a proximal radius 242*b*. The retention feature 242 can be tapered between the distal radius 242*a* and the proximal radius 242*b*. As illustrated, the distal radius 242*a* is smaller than the proximal radius 242*b*.

Upon insertion of the IV spike 210, the proximal radius 242*b* of the retention feature 242 can engage against the membrane of the IV container. Advantageously, the proximal radius 242*b* of the retention feature 242 can provide a greater surface area to engage the membrane of the IV container to prevent the removal of the IV spike 210 from the IV container. In some applications, the retention features 242 can enlarge the puncture site as the IV spike 210 is introduced.

In the depicted example, the retention features 242 can be overmolded or formed of a compliant material, such as a soft polymer, a thermoplastic elastomer (TPE) and/or silicone. In some embodiments, the retention features 242 can be formed from a material with a greater compliance (lower durometer) than the material of the spike body 220.

Optionally, the retention features 242 can be formed from a same or similar material as the spike body 220. In some embodiments, the retention features 242 are integrally formed with the spike body 220.

Figure 6:
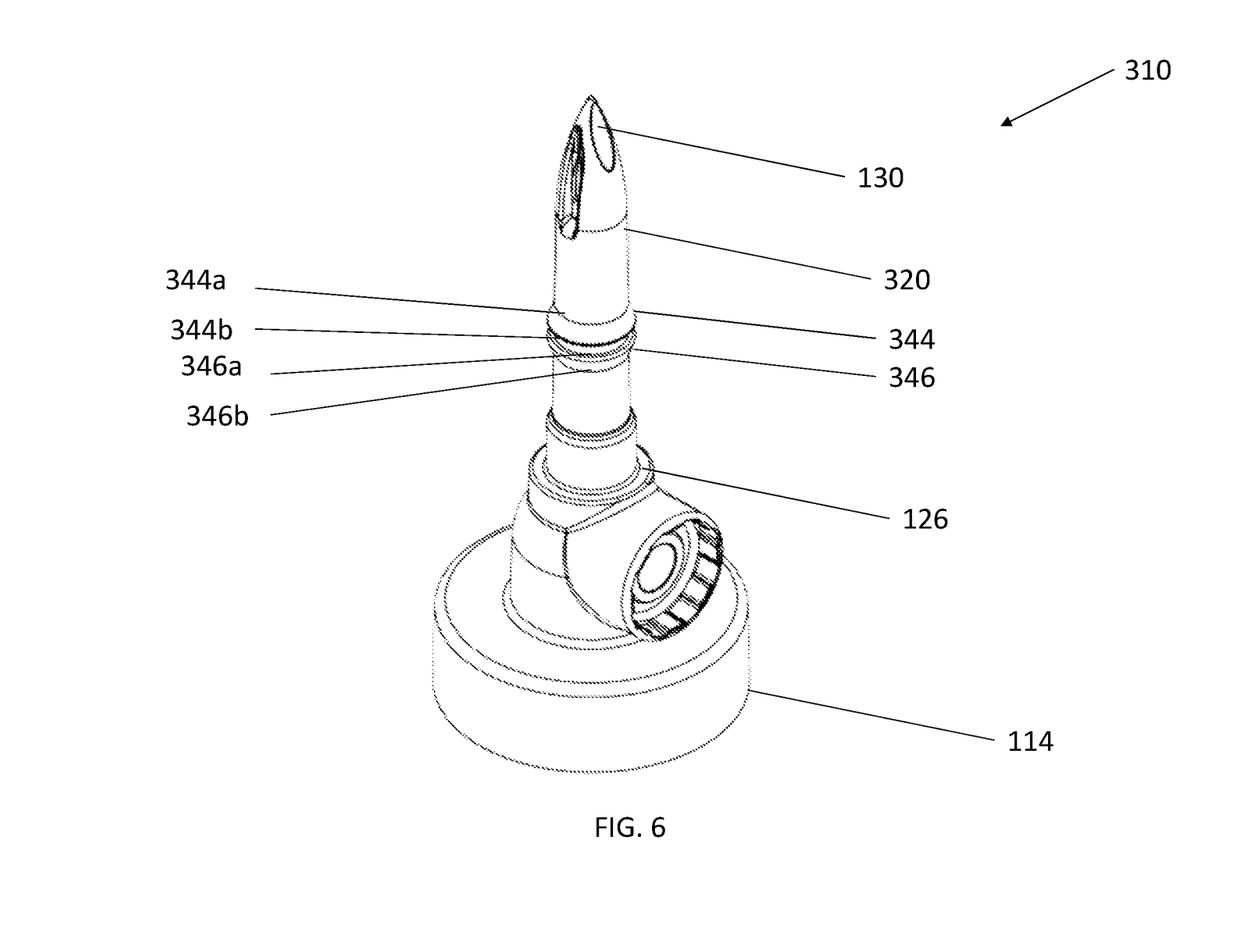
FIG. 6 is a perspective view of an IV spike for use with the IV set of FIG. 1, in accordance with various aspects of the present disclosure.

FIG. 6 is a perspective view of an IV spike 310 for use with the IV set 100 of FIG. 1, in accordance with various aspects of the present disclosure. In the depicted example, the IV spike 310 includes an upper retention feature, barb, or chamfer face 344 and a lower retention feature, barb, or chamfer face 346 that cooperatively create a physical barrier that prevent the removal of the IV spike 310 from the IV container.

In some embodiments, the upper retention feature 344 and the lower retention feature 346 extend radially away from the spike body 320. In the depicted example, the upper retention feature 344 and the lower retention feature 346 each have a tapered shape. As illustrated, the upper retention feature 344 and the lower retention feature 346 can be axially spaced apart.

In the depicted example, the upper retention feature 344 includes an upper distal radius 344*a* and an upper proximal radius 344*b*. The upper retention feature 344 can be tapered between the upper distal radius 344*a* and the upper proximal radius 344*b*. As illustrated, the upper distal radius 344*a* is smaller than the upper proximal radius 344*b*. In some embodiments, the smaller upper distal radius 344*a* of the upper retention feature 344 allows the upper retention feature 344 to pass through the puncture site.

Similarly, the lower retention feature 346 includes a lower distal radius 346*a* and a lower proximal radius 346*b*. The lower retention feature 346 can be tapered between the lower distal radius 346*a* and the lower proximal radius 346*b*. As illustrated, the lower distal radius 346*a* is larger than the lower proximal radius 346*b*.

Upon insertion of the IV spike 310, the upper proximal radius 344*b* of the upper retention feature 344 can engage against the membrane of the IV container. Similarly, the lower distal radius 346*a* of the lower retention feature 346 can engage against the opposite side of the membrane of the IV container, allowing the membrane to be retained (creating a "hard stop") between the upper retention feature 344 and the lower retention feature 346 to prevent the removal of the IV spike 310 from the IV container. In some embodiments, the use of the upper retention feature 344 and the lower retention feature 346 permits for the reuse of an IV container with the IV spike 310.

In the depicted example, the upper retention feature 344 and the lower retention feature 346 can be overmolded or formed of a compliant material, such as a soft polymer, a thermoplastic elastomer (TPE) and/or silicone. In some embodiments, the upper retention feature 344 and the lower retention feature 346 can be formed from a material with a greater compliance (lower durometer) than the material of the spike body 320.

Optionally, the upper retention feature 344 and the lower retention feature 346 can be formed from a same or similar material as the spike body 320. In some embodiments, the upper retention feature 344 and the lower retention feature 346 are integrally formed with the spike body 320.

Figure 7:
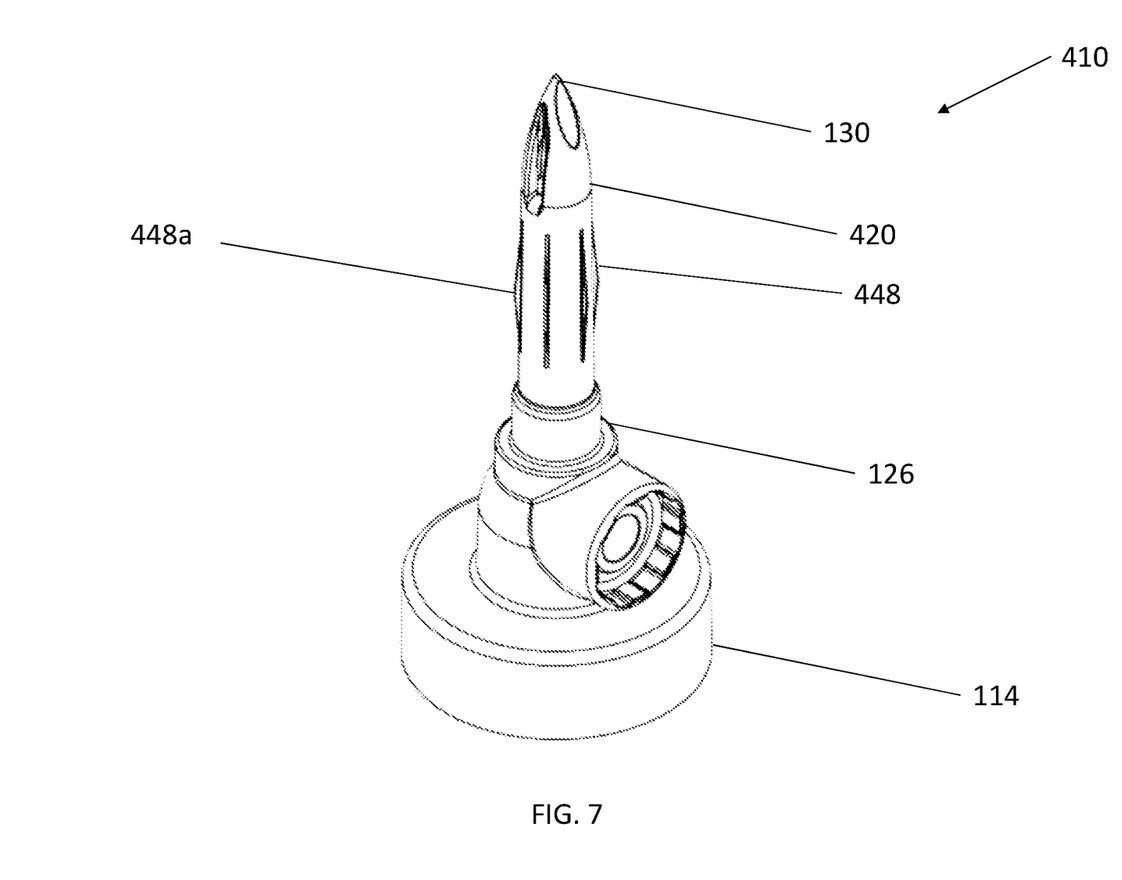
FIG. 7 is a perspective view of an IV spike for use with the IV set of FIG. 1, in accordance with various aspects of the present disclosure.

FIG. 7 is a perspective view of an IV spike 410 for use with the IV set 100 of FIG. 1, in accordance with various aspects of the present disclosure. In the depicted example, the IV spike 210 includes axial retention features 448 that create a physical barrier that prevent the removal of the IV spike 410 from the IV container.

In some embodiments, the axial retention features 448 extend axially along and radially away from the spike body 420. In the depicted example, the axial retention features 448 have a ribbed shape that smoothly tapers to a central radial height 448*a* that allows the axial retention features 448 to pass through the puncture site. In some embodiments, the axial retention features 448 can be radially spaced apart.

Upon insertion of the IV spike 410, the taper of the axial retention features 448 can engage against the membrane of the IV container. Advantageously, axial retention features 448 can provide a greater surface area to engage the membrane of the IV container to prevent the removal of the IV spike 410 from the IV container.

In the depicted example, the axial retention features 448 can be overmolded or formed of a compliant material, such as a soft polymer, a thermoplastic elastomer (TPE) and/or silicone. In some embodiments, the axial retention features 448 can be formed from a material with a greater compliance (lower durometer) than the material of the spike body 420.

Optionally, the axial retention features 448 can be formed from a same or similar material as the spike body 420. In some embodiments, the axial retention features 448 are integrally formed with the spike body 420.

In some embodiments, the IV spikes described herein can include one or more or any combination of the retention features described herein. Additionally, and without limitation, additional retention features can include O-rings, toroidal engagement features, spherical protrusions or engagement features, and/or spikes. Optionally, an IV spike can include retention features that are manipulated by the clinician or by introducing the IV spike to the IV container. For example, an IV spike can include a movable collar, a rotating cam assembly, or a movable oblong retention feature. In some embodiments, an IV spike can include retention features that are expandable after inserting the IV spike into the IV container. For example, an IV spike can include an expandable spike body, and/or a fluid absorbable retention feature. In some embodiments, an IV spike can include external retention features, including, but not limited to outer retainers that engage an outer surface of an IV container and/or hooks that engage an outer surface of an IV container.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An IV spike, comprising:
a spike body comprising a first material and a spike portion converging to a point;
at least one spike flow port formed through the spike body;
a lower flow port in fluid communication with the at least one spike flow port; and
an overmolded engagement feature disposed around the spike body and extending radially away from the spike body, wherein the overmolded engagement feature comprises:
a second material;
an upper barb with an upper axially distal radius and an upper axially proximal radius, wherein the upper barb tapers from the smaller upper axially distal radius to the larger upper axially proximal radius; and
a lower barb with a lower axially distal radius and a lower axially proximal radius, wherein the lower barb tapers from the larger lower axially distal radius to the smaller lower axially proximal radius and the lower barb is axially spaced apart from the upper barb, and wherein the overmolded engagement feature is configured to retain the IV spike within an IV container.

2. The IV spike of claim 1, wherein the first material comprises acrylonitrile butadiene styrene plastic.

3. The IV spike of claim 1, wherein the spike portion comprises a bevel.

4. The IV spike of claim 1, wherein the at least one spike flow port is disposed adjacent to the spike portion.

5. The IV spike of claim 1, wherein the at least one spike flow port comprises a plurality of flow ports.

6. The IV spike of claim 1, wherein the second material comprises a greater coefficient of friction than the first material.

7. The IV spike of claim 1, wherein the second material comprises a thermoplastic elastomer or silicone.

8. The IV spike of claim 1, wherein the overmolded engagement feature comprises a cylindrical body.

9. The IV spike of claim 8, wherein the overmolded engagement feature is disposed circumferentially around the spike body.

10. The IV spike of claim 1, wherein the overmolded engagement feature comprises an axial retention feature with a central height extending radially away from the spike body.

11. A method to transfer fluid from an IV container to a drip chamber, the method comprising:
   engaging an overmolded engagement feature of an IV spike against a membrane of the IV container, wherein the overmolded engagement feature comprises:
      a material different than the IV spike;
      an upper barb with an upper axially distal radius and an upper axially proximal radius, wherein the upper barb tapers from the smaller upper axially distal radius to the larger upper axially proximal radius; and
      a lower barb with a lower axially distal radius and a lower axially proximal radius, wherein the lower barb tapers from the larger lower axially distal radius to the smaller lower axially proximal radius, wherein the membrane of the IV container is axially disposed between the upper barb and the lower barb; and
   directing flow from the IV container to the drip chamber through the IV spike.

12. The method of claim 11, further comprising:
   piercing the IV container by advancing the IV spike through the membrane of the IV container; and
   advancing the IV spike into the IV container.

* * * * *